United States Patent [19]

Hopson

[11] 4,224,698
[45] Sep. 30, 1980

[54] ACETABULAR CUP FOR TOTAL HIP REPLACEMENTS

[76] Inventor: Clark N. Hopson, 3738 Broadview Dr., Cincinnati, Ohio 45208

[21] Appl. No.: 27,489

[22] Filed: Apr. 5, 1979

[51] Int. Cl.³ .............................................. A61F 1/24
[52] U.S. Cl. .................................. 3/1.912; 128/92 C
[58] Field of Search ................... 3/1.912, 1.913, 1.91; 128/92 C

[56] References Cited

U.S. PATENT DOCUMENTS

| | | | |
|---|---|---|---|
| 3,829,904 | 8/1974 | Ling et al. | 3/1.912 |
| 4,123,806 | 11/1978 | Amstutz et al. | 3/1.912 |
| 4,153,953 | 5/1979 | Grobbelaar | 3/1.912 X |

Primary Examiner—Ronald L. Frinks
Attorney, Agent, or Firm—Frost & Jacobs

[57] ABSTRACT

An acetabular cup for total hip replacements is disclosed which provides radiographically opaque elements for the two halves of the periphery of the cup, said opaque elements having different configurations so that it is possible from an anterior-posterior radiographic view to determine whether the cup is facing anteriorly or posteriorly.

3 Claims, 5 Drawing Figures

ACETABULAR CUP FOR TOTAL HIP REPLACEMENTS

BRIEF SUMMARY OF THE INVENTION

The invention relates to an acetabular cup for total hip replacements. The acetabular cup in effect constitutes a new lining for the acetabulum in the pelvis of the patient. When a total hip replacement becomes necessary because of arthritis or other reason, an operation is performed by an orthopaedist which involves a reaming of the acetabulum to enlarge it to receive the acetabular cup. The cup is cemented into the reamed out acetabulum and the femoral neck is removed and the femur is reamed out to receive the femoral prosthesis which terminates in a ball adapted to engage in the acetabular cup. In another procedure which is sometimes used, the existing femoral head is merely reshaped and capped, rather than being replaced.

Because the conventional acetabular cup prosthesis is made of a plastic material, it is pervious to X-rays and originally it was impossible to determine the position of the acetabular cup from an examination of a radiographic view.

This problem was sought to be overcome by providing a wrap of wire embedded in a groove around the periphery of the open end of the cup. This wire of metallic material was impervious to X-rays and would therefore show up on a radiographic view. However, it would show up in an anterior-posterior view as an oval and it was impossible to tell whether the cup was facing anteriorly or posteriorly.

According to the present invention, this problem is overcome by providing a radiographically opaque element over one-half of the periphery of the cup which differs in configuration from a radiographically opaque material on the other half of the periphery of the cup.

DETAILED DESCRIPTION

Figure 1:
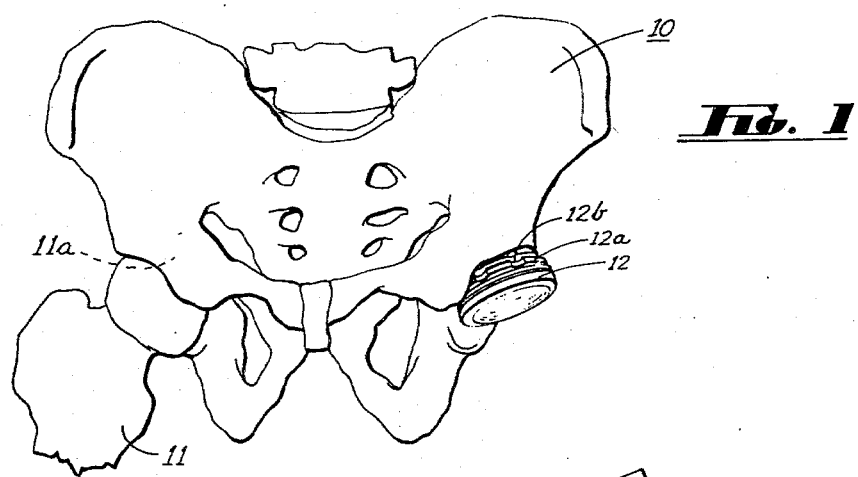
FIG. 1 is an anterior-posterior view of a skeletal pelvis with a cup according to the invention placed in the left acetabulum.
Figure 2:
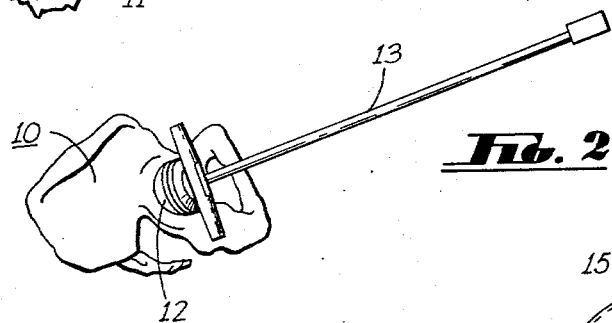
FIG. 2 is a fragmentary view of a pelvis showing a typical tool for placement of the acetabular cup in the acetabulum.
Figure 3:
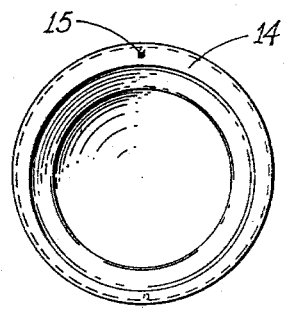
FIG. 3 is a front view of a cup according to the invention.

Referring first to FIG. 1, the numeral 10 represents a skeletal pelvis in an anterior-posterior view. The right femur 11 is shown seated in the right acetabulum 11a. A prosthesis or acetabular cup 12 is shown in place in the left acetabulum.

The cup itself is conventional and is provided with grooves 12a and cross-grooves 12b to provide a lock when the acetabular cup is cemented in place in the reamed out acetabulum.

The details of the method of emplacement and orientation of the acetabular cup in the reamed out acetabulum does not form a part of this invention and may be conducted in accordance with procedures well known among orthopaedic surgeons.

The cup basically is a hemispherical element, the walls of which at the upper end, as indicated at 14, are sometimes thicker than at the sides or bottom because it is at the top where the main weight of the body is carried in use. A locating hole 15 is provided at the center of the top front face of the cup to be engaged by the tool 13 so that the cup may be rotated and swiveled to the proper desired position.

Figure 4:
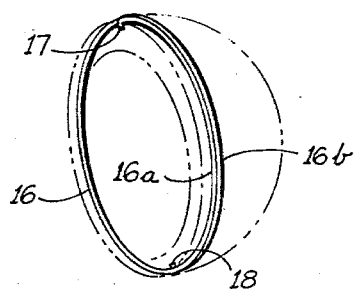
FIGS. 4 and 5 are views of the cup as they would appear in an anterior-posterior X-ray and showing how the invention makes it possible to determine whether the cup is facing anteriorly or posteriorly.
Figure 5:
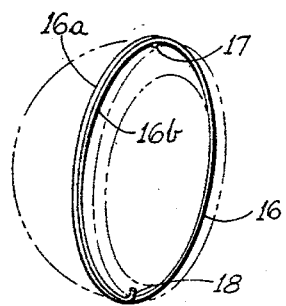

The best mode of practicing the invention involves the wrapping of one and one-half turns of wire 16 in a spiral groove around the periphery of the face of the cup. One end of the wire is fixed in the cup opposite the locating hole 15 as indicated in FIGS. 4 and 5 at 17. The other end of the wire is fixed in the cup diametrically opposite the point 17 as indicated at 18 in FIGS. 4 and 5.

From a comparison of FIGS. 4 and 5, it will be seen that the one and one-half turns of wire 16, which will show up on a radiographic view as an oval, will have a single wire on the one side indicated at 16, and two wires side-by-side on the opposite side indicated at 16a and 16b. The same reference numerals have been applied in FIG. 5 and very clearly these views show that a differentiation is provided to show whether the cup is facing anteriorly or posteriorly.

While a single wire with one and one-half turns has been shown, it will be clear to those skilled in the art that if desired a single wire could be used for one-half the circumference and two separate wires for the other half, or that a wire could be used for one-half of the circumference and a series of small radiographically opaque beads could be embedded in the other side. The important thing is simply to be able to differentiate between what is seen in a radiographic view as between the two halves of the periphery of the acetabular cup.

It will be clear that numerous modifications may be made without departing from the spirit of the invention and therefore no limitation which is not specifically expressed in the claims is intended and no such limitation should be implied.

I claim:

1. In an acetabular cup for total hip replacement, having a locating hole in the face of said cup at the top; a radiographic marker system making possible the determination from an anterior-posterior radiographic view of the hip whether the cup is facing anteriorly or posteriorly, comprising a radiographically impervious element along one half of the open periphery of said cup beginning opposite said locating hole, and a radiographically impervious element along the other one half of the periphery of said cup, the configuration of the impervious elements along the two halves of the open periphery of said cup being different, allowing differentiation by X-ray of the anterior and posterior halves of the cup.

2. A device according to claim 1, wherein the impervious element along one half of the periphery is a single metallic wire, and the impervious element along the other half of the periphery comprises two metallic wires side-by-side.

3. A device according to claim 1, wherein the impervious element comprises a metallic wire making one and one-half turns around the periphery of said cup.

* * * * *